United States Patent
Bathula et al.

(10) Patent No.: US 8,012,952 B2
(45) Date of Patent: Sep. 6, 2011

(54) CATIONIC 17 α-SUBSTITUTED-ESTRADIOL DERIVATIVES USEFUL AS ANTI-CANCER AGENT

(75) Inventors: Surendar Reddy Bathula, Andhra Pradesh (IN); Rajkumar Banerjee, Andhra Pradesh (IN)

(73) Assignee: Council of Scientific & Industrial Research, New Delhi (IN)

( * ) Notice: Subject to any disclaimer, the term of this patent is extended or adjusted under 35 U.S.C. 154(b) by 193 days.

(21) Appl. No.: 12/294,229

(22) PCT Filed: Dec. 31, 2007

(86) PCT No.: PCT/IN2007/000615
§ 371 (c)(1), (2), (4) Date: Sep. 23, 2008

(87) PCT Pub. No.: WO2008/099414
PCT Pub. Date: Aug. 21, 2008

(65) Prior Publication Data
US 2009/0062230 A1    Mar. 5, 2009

(30) Foreign Application Priority Data
Feb. 13, 2007   (IN) .............................. 278/DEL/2007

(51) Int. Cl.
*A61K 31/56* (2006.01)
*C07J 3/00* (2006.01)

(52) U.S. Cl. ........................................ 514/182; 552/610
(58) Field of Classification Search .................. 514/182; 552/610
See application file for complete search history.

*Primary Examiner* — Marcos L Sznaidman
(74) *Attorney, Agent, or Firm* — DLA Piper LLP (US)

(57) ABSTRACT

The present invention provides a novel series of cationic, lipid-based, 17α-substituted-estradiol derivatives. The present invention further provides a process for the preparation of a novel series of 17α-substituted-estradiol derivatives. The invention also provides information about highly selective anticancer activities of these molecules in estrogen responsive cell lines. The compound elicits high level of toxicity to gynecological cancer cell lines such as MCF-7, T47D (estrogen receptor positive cell lines), MDA-MB-468 (estrogen receptor knock-out cell line), HeLa (cervical cancer). The present class of cationic lipid-based, estradiol derivatives is likely to find specific use in developing target specifically deliverable anticancer drugs for the treatment of gynecological cancers that are most prevalent in women population irrespective of ethnicity.

16 Claims, 5 Drawing Sheets

A

B

A

B

CATIONIC 17 α-SUBSTITUTED-ESTRADIOL DERIVATIVES USEFUL AS ANTI-CANCER AGENT

CROSS REFERENCE TO RELATED APPLICATIONS

This application is a 35 USC §371 National Stage application of International Application No. PCT/1N2007/000615 filed Dec. 31, 2007, now pending; which claims the benefit under 35 USC §119(a) to India Patent Application No. 278/DEL/2007 filed Feb. 13, 2007. The disclosure of each of the prior applications is considered part of and is incorporated by reference in the disclosure of this application.

FIELD OF THE INVENTION

The present invention relates to novel cationic 17α substituted estradiol derivative useful as anti cancer agent. Particularly, the present invention relates to a novel series of cationic lipid-based, derivatives of estradiol, which is the natural ligand for estrogen receptors. More particularly, the present invention relates to novel cationic 17α substituted estradiol derivative of formula A

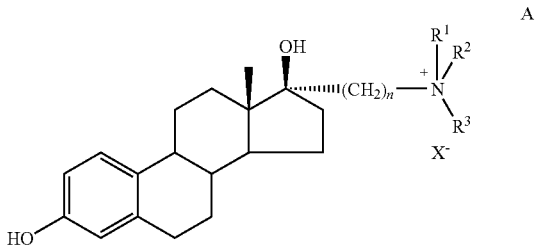

wherein:
each of $R^1$ and $R^2$ is independently hydrogen or a lipophilic moiety containing at least two carbon atoms and is selected from 2-22 carbon containing alkyl, mono-, di- and tri-unsaturated alkenyl ($C_2$-$C_{22}$) provided both $R^1$ and $R^2$ are not hydrogen; $R^3$ is independently hydrogen or $C_1$-$C_5$, straight or branched chain alkyl group; n is an integer varies from 2 to 7; and X is selected from chlorine, bromine or iodine atom.

The present invention also relates to a process for the preparation of novel cationic 17α substituted estradiol derivative of formula A. The invention provides information about highly selective anticancer activities of these molecules in estrogen responsive cell lines. The area of medical science that is likely to benefit most from the present invention is targeted cancer therapy.

BACKGROUND AND PRIOR ART OF THE INVENTION

Chemotherapy and radiation therapies are two current clinical modalities commonly used for the treatment of cancer. Mostly these techniques are effective to block the growth of tumor. However, there is often a recurrence of the disease, possibly because of incomplete cell killing or cells acquiring drug resistance. There is also an added disadvantage of non-specific accumulation and killing of normal cells leading to irreparable cytotoxicity in humans. This is mainly because cytotoxic drugs generally do not posses targeting property. The need of the hour is to develop newer drugs which will be targeted to cancers of certain specific origin by utilizing the cancer specific molecular targets, such as, utilizing breast cancer specific proteins, e.g., estrogen receptor, for targeting and killing breast cancer cells.

Estrogen receptor (ER) is a nuclear hormone receptor residing in mostly gynecological cells mainly, breast, uterus, and ovary cells that bear both cancerous and non-cancerous phenotype. The ER is also found to express avidly in vascular endothelial cells wherein it regulates the production of nitric oxide synthases and hence directly help in the positive production and regulation of vascular endothelial growth factors (VEGF) (3). The VEGF is one of the well-known angiogenic factors for the sustained growth of tumor mass.

ER has two subtypes α and β. This receptor, a ligand activated transcription factor upon activation translocates itself into the nucleus. Classically, as a homodimer it binds to specific DNA sequences called Estrogen response elements (ERE) and positively or negatively regulates transcription of target genes. In breast cancer cells ER regulates cancer up-regulating genes such as BCl-2, BRCA-1, and VEGF through ERE-promoter activation of respective genes (1). Therefore, ER is a positive regulator of cancer causing effects and hence ER serves as a very useful target for treating cancer through designing novel ER-targeted therapeutics.

Recently, we have shown that the estrogen the natural ligand to ER, when attached to stealth, cationic liposomal system, mediates anti-cancer gene delivery to breast cancer cells in a target specific manner (2). Estradiol, the endogenous ligand for ER is chemically modified to modulate the ER function which is of high importance for containing variety of diseases including breast cancer and osteoporosis. During the primary stage, i.e., estrogen responsive phase the breast cancer can be successfully contained through chemotherapeutic management. A variety of structural modification and several proactive chemical moieties are included in 17-beta estradiol to develop new generation drugs for the treatment of breast cancer and osteoporosis. There are several examples that can be cited towards this effect: 17α-alkynyl conjugate of estradiol that links between an enediyne system to that of steroidal moiety, possesses comparable ER affinity to estradiol. The compound tentatively acts as anti-cancer, targeted, prodrug through generation of diyl radicals produced by the cycloaromatization of enediyne systems which are known classes of antitumor agents (4). 17-alkylestradiols with alkyl group size is widely varied for their carbon chains from methyl to dodecyl, are also synthesized and tested to find excellent inhibitory effect against steroid sulfatase, the enzyme that is responsible for conversion of sulfated estrogens into free estrogens in normal and cancer cells (5). 17-α azido-alkynyl group containing estradiol is found to possess ER agonistic property (6). C-16 position of estradiol is also utilized for synthesizing ER targeting antagonist/agonists. The C-16 position has been introduced with a carbon chain length and amide bond to induce anti-estrogenic property (7). Synthetic analogues of 2-methoxy estradiol (2-ME2), the endogenous mammalian metabolite of natural hormone estradiol, are also extensively synthesized and studied to find elevated antimitotic activity compared to what is naturally possessed by the metabolite 2-ME2 itself (8-12). An aniline mustard conjugate at 7-α position of estradiol is developed that possess genotoxicity to only ER positive cells through formation of covalent DNA adducts in those cells (13).

The present invention relates to development of a novel series of estrogen receptor binding chemical compounds that contain 17α-estradiol and cationic twin chain lipid moieties. The delivery induced anti-cancer properties of this new class of cationic estradiol described herein is remarkably cell tropic for only gynecological cancer cells, especially, breast cancer cells and also cervical cancer cell. The cellular toxicity of this class of molecules is minimal to null in case of non-gynecological cancer cells and in cells of non-cancerous lineage. This indicates that the cellular toxicity in respective cells is probably mediated through estrogen receptors which are highly implicated in gynecological cancer phenotypes. Thus, the present class of cationic estradiol derivative is likely to find future applications in anticancer therapy for cancers that are implicated with estrogen receptors. Moreover, the present class of compound has cationic moiety in their structure and that the cationic group with optimized length of carbon-chain may have aggregative property as that of cationic liposomes, which may help the molecule to bind with DNA (a polyanionic biologically important macromolecule). So, the present class of molecule may act as a DNA delivery agent to the cancer cells implicated with ER for the purpose of treating cancers and the references may be made to Carolyn M. Klinge. *Nucleic Acid Research*, 2001, 29, 2905-2919; Reddy B. S. and Banerjee R. *Angewandte Chemie Int. Ed.*, 2005, 44, 6723-6727; Ken L. Chambliss and Philip W. Shaul, *Endocrine Review*, 2006, 23, 665-686; Jones et. al. *J. Org. Chem.*, 2001; 66, 3688-3694, and ref. 11 therein; Boivin et. al. *J. Med. Chem.*, 2000, 43, 4465-4478; Kasiotis et. al. *Steroids*, 2006, 71, 249-255; Pelletier et. al. *Steroids*, 1994, 59, 536-547; Rao et. al. *Steroids*, 2002, 67, 1079-1089; Cushman et. al. *J. Med. Chem.*, 1995, 38, 2041-2049; Sachdeva Y. et. al. World Patent No. 9840398, 1998; Purohit A et. al. *Int. J. Cancer* 2000, 85, 584-589; Brueggemeier R. W. et. al. *J. Steroid Biochem Mol Biol* 2001, 78, 145-156; Mitra et. al. *J. Am. Chem. Soc.* 2002, 124, 1862-1863; Jain P T, Seth P, Gewirtz D A *Biochim Biophys Acta*, 1999, 1451, 224-232; Jain P T, Gewirtz D A, *J. Mol. Med.*, 1998, 76, 709-714.

SUMMARY OF INVENTION

Accordingly the present invention provides a novel cationic estradiol derivative having the general formula A

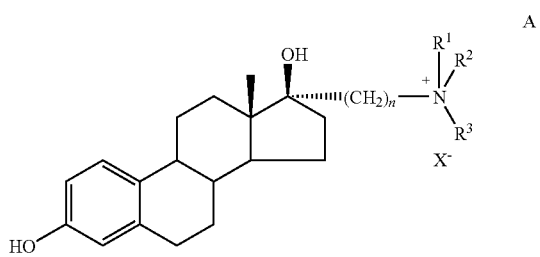

wherein:
each of $R^1$ and $R^2$ is independently hydrogen or a lipophilic moiety containing at least two carbon atoms and is selected from 2-22 carbon containing alkyl, mono-, di- and tri-unsaturated alkenyl ($C_2$-$C_{22}$) provided both $R^1$ and $R^2$ are not hydrogen; $R^3$ is independently hydrogen or $C_1$-$C_5$, straight or branched chain alkyl group; n is an integer varies from 2 to 7; and X is selected from chlorine, bromine or iodine atom.

In an embodiment of the present invention, each of $R_1$ and $R_2$ is independently hydrogen or an aliphatic hydrocarbon chain provided both $R_1$ and $R_2$ are not hydrogen.

In another embodiment of the present invention, both $R_1$ and $R_2$ are aliphatic hydrocarbon chains.

In still another embodiment of the present invention, $R_3$ is $C_1$-$C_5$, straight or branched chain alkyl group or hydrogen atom when $R_1$ and $R_2$ are independently hydrogen or an aliphatic hydrocarbon chains provided both $R_1$ and $R_2$ are not hydrogen.

In yet another embodiment of the present invention, $R_3$ is an alkyl group and both $R_1$ and $R_2$ are aliphatic hydrocarbon chains.

In yet another embodiment of the present invention, $R_3$ is a hydrogen atom and both $R_1$ and $R_2$ are aliphatic hydrocarbon chains.

In yet another embodiment of the present invention, the representative compounds of formula A are as follows:

17α-[3-N,N-dioctyl(methyl)aminopropane]-17β-Estradiol (1);

17α-[3-N,N-dihexadecyl(methyl)aminopropane]-17β-Estradiol (2) and

17α-[3-N,N-diethyl(methyl)aminopropane]-17β-Estradiol (3)

In yet another embodiment of the present invention, the compound exhibits in-vitro cytotoxicity to gynecological cancer cell lines derived from cancer cell lines selected from the group consisting of MCF-7, T47D (estrogen receptor positive cell lines), MDA-MB-468 (estrogen receptor knock-out cell line), Hela (cervical cancer).

In yet another embodiment of the present invention, 17α-[3-N,N-dioctyl(methyl)aminopropane]-17β-Estradiol (1) exhibit in-vitro percent cell viability in the range of 2-10% for cancer cell lines selected from the group consisting of MCF-7, T47D, Hela and MDA-MB-468 at 50 μM concentration of the said compound after 4 hrs of treatment and 6 days of assay period.

The present invention further provides a pharmaceutical composition comprising:
a) a cationic estradiol derivative,
b) a co-lipid, and
c) a polyanionic compound optionally with pharmaceutically acceptable carrier, adjuvant or additives In an embodiment the pharmaceutical composition comprising:
a. a cationic estradiol derivative,
b. a co-lipid, and
c. a polyanionic compound optionally along with a pharmaceutically acceptable carrier, adjuvant or additives exhibits in-vitro cytotoxicity to gynecological cancer cell lines derived from cancer cell types selected from the group consisting of MCF-7, T47D (estrogen receptor positive cell lines), MDA-MB-468 (estrogen receptor knock-out cell line), Hela (cervical cancer).

In yet another embodiment of the present invention, the molar ratio of cationic estradiol derivative to co-lipid is about 1:1.

In yet another embodiment of the present invention, the molar ratio of total lipid comprising cationic estradiol derivative and co-lipid to poly anionic compound (DNA) is in the range of 1:1 to 8:1.

In yet another embodiment of the present invention, cationic estradiol derivative used comprising a compound of general formula A

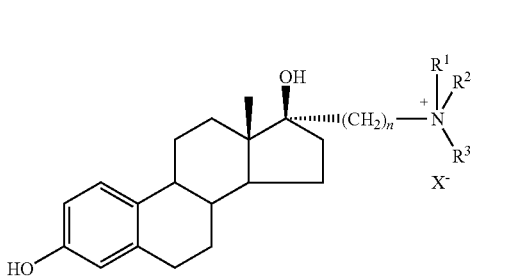

wherein:

each of $R^1$ and $R^2$ is independently hydrogen or a lipophilic moiety containing at least two carbon atoms and is selected from 2-22 carbon containing alkyl, mono-, di- and tri-unsaturated alkenyl ($C_2$-$C_{22}$) provided both $R^1$ and $R^2$ are not hydrogen; $R^3$ is independently hydrogen or $C_1$-$C_5$, straight or branched chain alkyl group; n is an integer varies from 2 to 7; and X is selected from chlorine, bromine or iodine atom.

In yet another embodiment of the present invention, the co-lipid used is selected from the group consisting of cholesterol, dioleoylphosphatidylethanolamine (DOPE) and dioleoylphosphatidylcholine (DOPC).

In yet another embodiment of the present invention, the polyanionic compound used is capable of encoding therapeutically important protein, nucleic acid, an oligonucleotide, a peptide or a protein.

In yet another embodiment of the present invention, the polyanionic compound used is selected from the group consisting of ribosomal RNA, antisense polynucleotide of RNA or DNA, polynucleotide of genomic DNA, cDNA or mRNA.

In yet another embodiment of the present invention, the nucleic acid used is a circular or linear plasmid or ribonucleic acid.

The present invention further provides a process for the synthesis of novel cationic estradiol derivative having the general formula A:

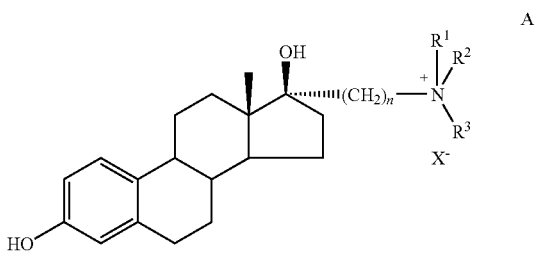

wherein:
each of $R^1$ and $R^2$ is independently hydrogen or a lipophilic moiety containing at least two carbon atoms and is optionally selected from 2-22 carbon containing alkyl, mono-, di- and tri-unsaturated alkenyl ($C_2$-$C_{22}$) provided both $R^1$ and $R^2$ are not hydrogen; $R^3$ is independently hydrogen or $C_1$-$C_5$, straight or branched chain alkyl group; n is an integer between 2 and 7; and X is optionally selected from chlorine, bromine or iodine atom; and the said process comprising the steps of:
a. preparing 3-tert-butyldimethylsilyloxy-17α-[3-aldehydo propane]-17β-estradiol from estrone by known method,
b. reacting the above said aldehyde compound of 3-tert-butyldimethylsilyloxy-17α-[3-aldehydo propane]-17β-estradiol with mono- or di-alkyl amine in the presence of sodium cyanoborohydride, in a dry organic solvent to obtain the corresponding secondary or tertiary amine followed by reaction with alkyl halide in an organic solvent to obtain the resultant tertiary or quaternized amine respectively, characterized in that quaternization of the intermediate tertiary amine is carried out at a temperature ranging between −10° C. to 50° C.,
c. deprotecting the silyl protection of aromatic hydroxyl group of the above said tertiary or quaternized amine obtained in step (b) by known method followed by ion exchange chromatography using halide ion exchange resins to obtain the desired compound.

In yet another embodiment of the present invention, the mono or di-alkyl amine used has saturated or unsaturated aliphatic hydrocarbon chain.

In yet another embodiment of the present invention, the saturated or unsaturated aliphatic hydrocarbon chain of mono or di-alkyl amine used is selected from the group consisting of $C_2$ to $C_{22}$ hydrocarbon chain.

In yet another embodiment of the present invention, the hydrocarbon chain of the mono, di-alkyl amine used is selected from the group consisting of $C_2$ to $C_{22}$ hydrocarbon.

In yet another embodiment of the present invention, the organic solvent used in step (a) is selected from the group consisting of chloroform, dichloro methane and ethyl acetate.

In yet another embodiment of the present invention, the organic solvent used in step (b) is selected from the group consisting of dichloro methane, methanol and a mixture thereof.

In yet another embodiment of the present invention, the alkyl halide used in step (b) is selected from $C_1$ to $C_5$ alkyl halides.

In yet another embodiment of the present invention, the halide ion exchange resins used in step (c) is selected from the group consisting of chloride, bromide and iodide ion exchange resins.

In yet another embodiment of the present invention, the representative compounds of formula A obtained are as follows: 3

17α-[3-N,N-dioctyl(methyl)aminopropane]-17β-Estradiol (1);

17α-[3-N,N-dihexadecyl(methyl)aminopropane]-17β-Estradiol (2) and

17α-[3-N,N-diethyl(methyl)aminopropane]-17β-Estradiol (3)

BRIEF DESCRIPTION OF THE DRAWINGS

FIG. 7A depicts the DNA binding property of derivative 2. It summarizes the results from gel-retardation assay of lipid DNA complexes comprising derivative 2 (i.e., structure 2), cholesterol or DOPE as respective co-lipids and DNA. The derivative 2 and the respective co-lipids are in a molar ratio of 1:1. The total lipids to DNA mole ratios (or charge ratio +/−) were varied from 1:1 to 8:1 as shown in the gel picture using 0.4 μg of DNA. In the extreme right lane pure DNA was run.

FIG. 7B depicts the DNA binding property of derivative 3. It summarizes the results from gel-retardation assay of lipid DNA complexes comprising derivative 3 (i.e., structure 3), cholesterol or DOPE as respective co-lipids and DNA. The derivative 3 and the respective co-lipids are in a molar ratio of 1:1. The total lipids to DNA mole ratios (or charge ratio +/−) were varied from 1:1 to 8:1 as shown in the gel picture using 0.4 μg of DNA. In the extreme right lane pure DNA was run.

DETAILED DESCRIPTION OF THE INVENTION

Figure 1:
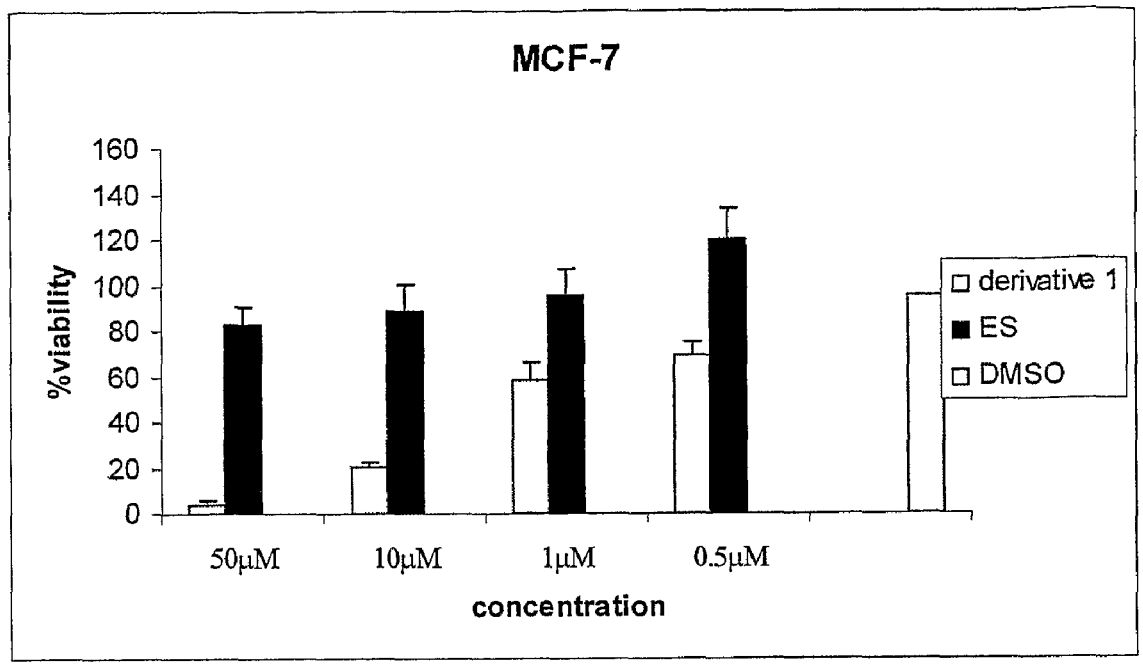
FIG. 1 summarizes the in vitro toxicity profile of derivative 1 in MCF-7 cells over a concentration variance of 0.5 μM to 50 μM in the presence of serum media. The cells were washed 4 h post treatment and were kept for 6 days and finally the viability was assayed with MTT. The toxicity profile is also compared with naked 17 β-estradiol and the maximum volume of DMSO that is used for treating naked derivative A in the serum media.

The present invention relates to process for the synthesis of a series of novel cationic estradiol derivatives and evaluation of their estrogen receptor-mediated anticancer activity in various human breast and cervical cancer cells. The novel cationic lipid based derivatives containing 17β-estradiol moiety acts as anticancer drugs that target specifically act upon cancer cells implicated directly/indirectly with estrogen receptors. The area of science that is likely to be benefited most from the present invention is targeted cancer therapy.

The distinctive novel structural features common to the cationic estradiol derivatives disclosed in the present invention include: (1) The presence of hydrophobic groups which are directly linked to the positively charged nitrogen atom and (2) the presence of estrogen receptor-binding 17β-estradiol group. It is believed that these unique structural features contribute significantly directly/indirectly to estrogen receptor-mediated anticancer activities of the novel cationic estradiol derivatives disclosed herein.

According to the practice of the present invention, "cationic" means the positive charge either on quaternized nitrogen or on a protonated nitrogen atom. The cationic characters of the present lipid-based derivatives may contribute to the enhanced, selective interaction of the lipid-based derivatives with cell constituents such as plasma membrane glycoproteins specifically in breast and cervical cancer cells. Although the reason of specificity arising from this angle is yet not deciphered but such enhanced interaction between the cationic lipid-based derivatives and cell membrane constituents may also play a key role in successfully transporting the intended therapeutic moiety that remains conjugated to the molecule, into the cancer cells.

The cationic estradiol derivative of the present invention has certain common structural and functional groups. As such, the said cationic estradiol derivative may be represented by the following generic formula (A):

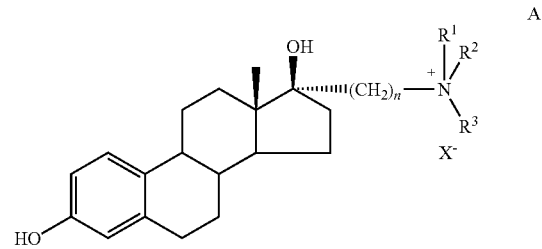

A wherein
each of $R^1$ and $R^2$ is independently hydrogen or a lipophilic moiety containing at least two carbon atoms and is optionally selected from 2-22 carbon containing alkyl, mono-, di- and tri-unsaturated alkenyl ($C_2$-$C_{22}$) provided both $R^1$ and $R^2$ are not hydrogen;
$R^3$ is independently hydrogen or alkyl ($C_1$-$C_5$, straight or branched);
n is an integer between 2 and 7
and X is selected from chlorine, bromine or iodine atom.

The cationic estradiol derivatives of the present invention have a lipophilic domain that may or may not facilitate the formation of lipid complexes or aggregates in aqueous solutions. However, the molecule because of the presence of estradiol moiety remains stably soluble in serum associated in vivo mimicking conditions. This is in conformity to the fact that estrogen, a predominantly hydrophobic molecule, freely moves out of ovary and swims through vascular and lymphatic bodies to intended organs such as breast and uterus by remaining as naturally 'pocketing-in' condition in blood serum proteins.

Exemplary lipophilic $R_1$ and $R_2$ groups include (1) saturated $C_2$-$C_{22}$ alkyl groups and (2) unsaturated $C_2$-$C_{22}$ alkenyl groups containing 1, 2, or 3 double bonds. In one preferred embodiment of the presently disclosed cationic lipids $R_1$=$R_2$=n-octyl, $R_3$ is a methyl, n=3, and $X^-$ is a chloride ion. Accordingly, the compound no. 1 is a representative example of the presently described novel cationic estradiol derivatives:

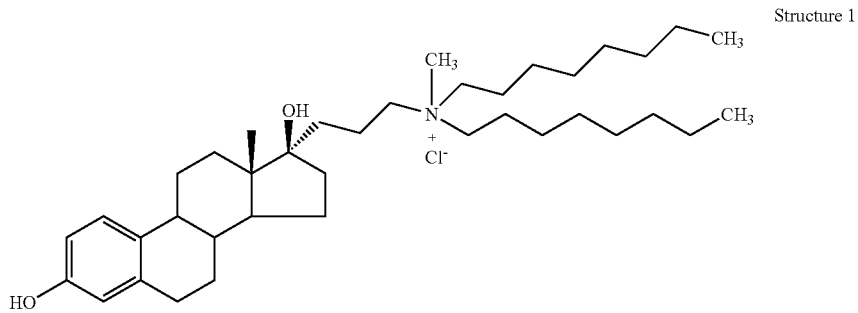

Structure 1

Syntheses of the Cationic Estradiol Derivatives
Scheme 1 outlines the synthetic strategy employed for preparing the representative cationic estradiol derivative 1 described in the present invention.
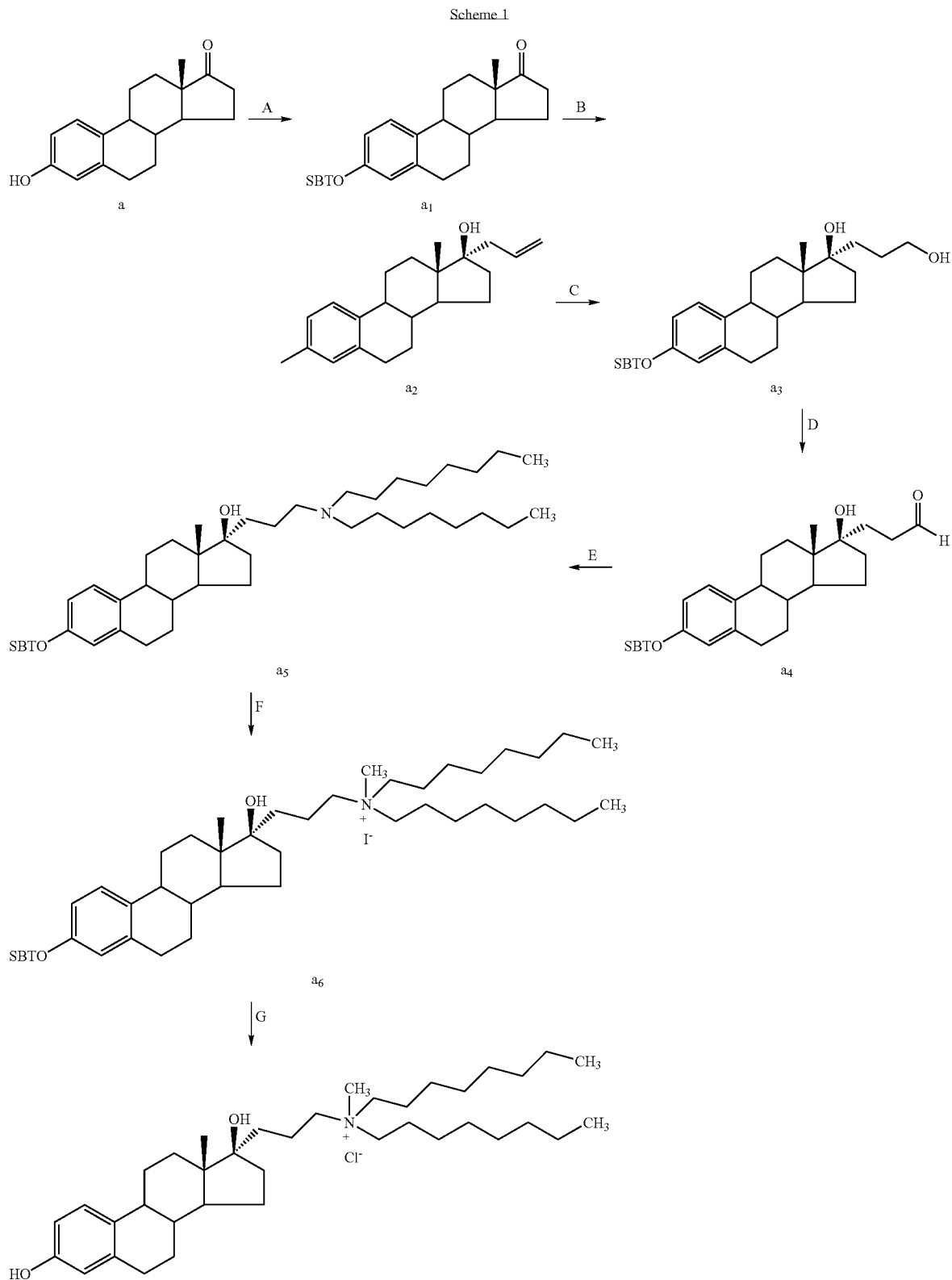
Scheme 1

A. Tert-butyl dimethylsilyl trifluoromethane sulphonate (TBDMS triflate), 2,6-lutidine, dry DCM
B. Mg, Allyl bromide, dry THF, 1,2-dibromoethane (as initiator)
C. Borane dimethylsulfide complex (BH$_3$.DMS), 3N NaOH, 30% H$_2$O$_2$, dry THF
D. Oxalyl chloride, DMSO, Triethylamine, −78° C., dry DCM
E. N,N-dioctyl amine, Sodium cyanoborohydride, Dry DCM
F. Methyl iodide, DCM+Methanol (1:1)
G. Tetra-n-butyl ammonium fluoride (TBAF), THF, Amberlyst A-26

Figure 2:
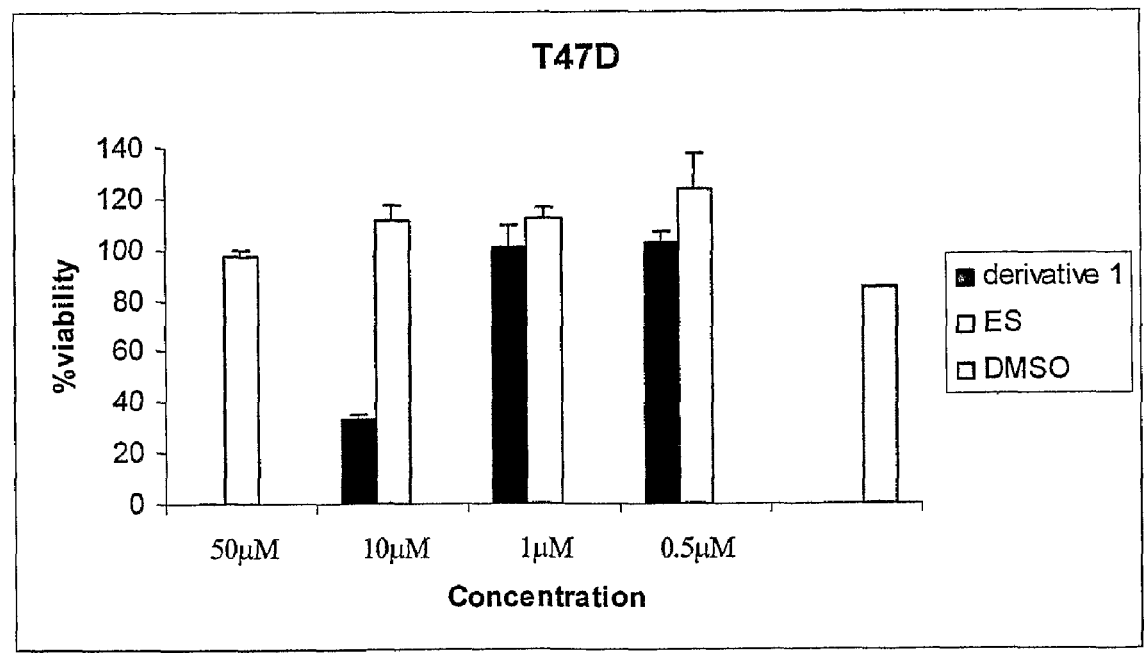
FIG. 2 summarizes the in vitro toxicity profile of derivative 1 in T47D cells over a concentration variance of 0.5 μM to 50 μM in the presence of serum media. The cells were washed 4 h post treatment and were kept for 6 days and finally the viability was assayed with MTT. The toxicity profile is also compared with naked 17 β-estradiol and the maximum volume of DMSO that is used for treating naked derivative A in the serum media.
Figure 3:
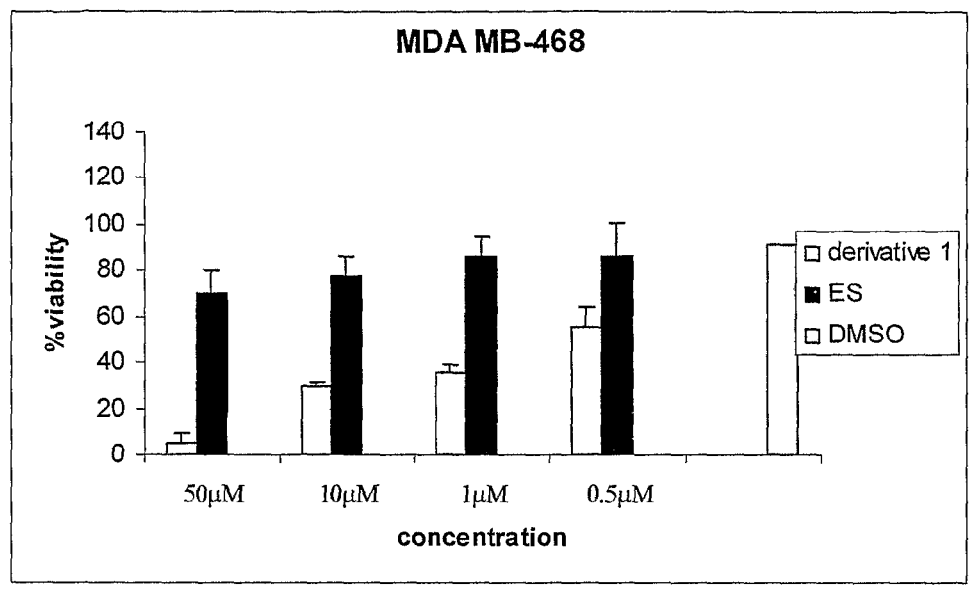
FIG. 3 summarizes the in vitro toxicity profile of derivative 1 in MDA-MB-468 cells over a concentration variance of 0.5 μM to 50 μM in the presence of serum media. The cells were washed 4 h post treatment and were kept for 4 days and finally the viability was assayed with MTT. The toxicity profile is also compared with naked 17 β-estradiol and the maximum volume of DMSO that is used for treating naked derivative A in the serum media.
Figure 4:
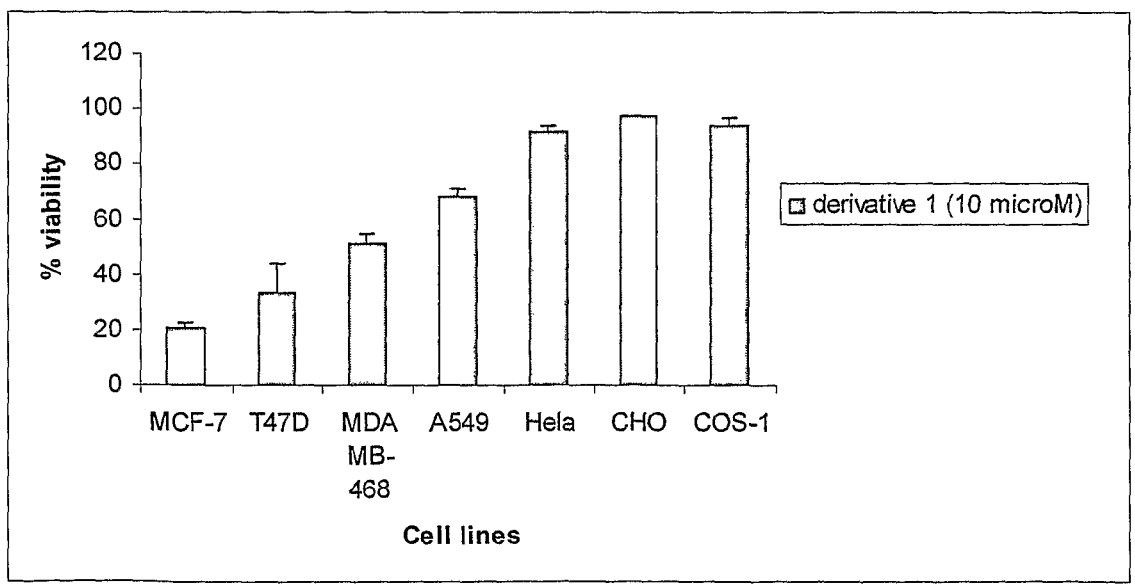
FIG. 4 summarizes the in vitro toxicity comparison of 10 μM of derivative 1 treated for 4 h in different cancer and non cancer cells. Following treatment the cells were washed and kept in serum media for 6 days and then assayed for viability with MTT.
Figure 5:
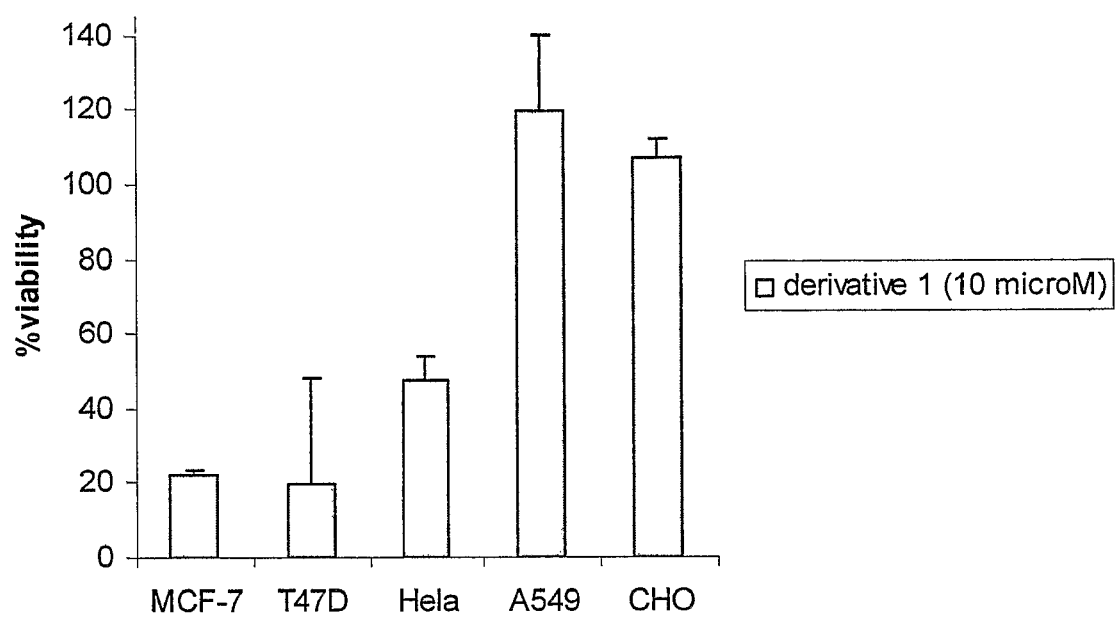
FIG. 5 summarizes the in vitro toxicity comparison of 10 μM of derivative 1 treated for 48 h in different cancer and non cancer cells. Following treatment the cells were washed and promptly assayed for viability with MTT.
Figure 6:
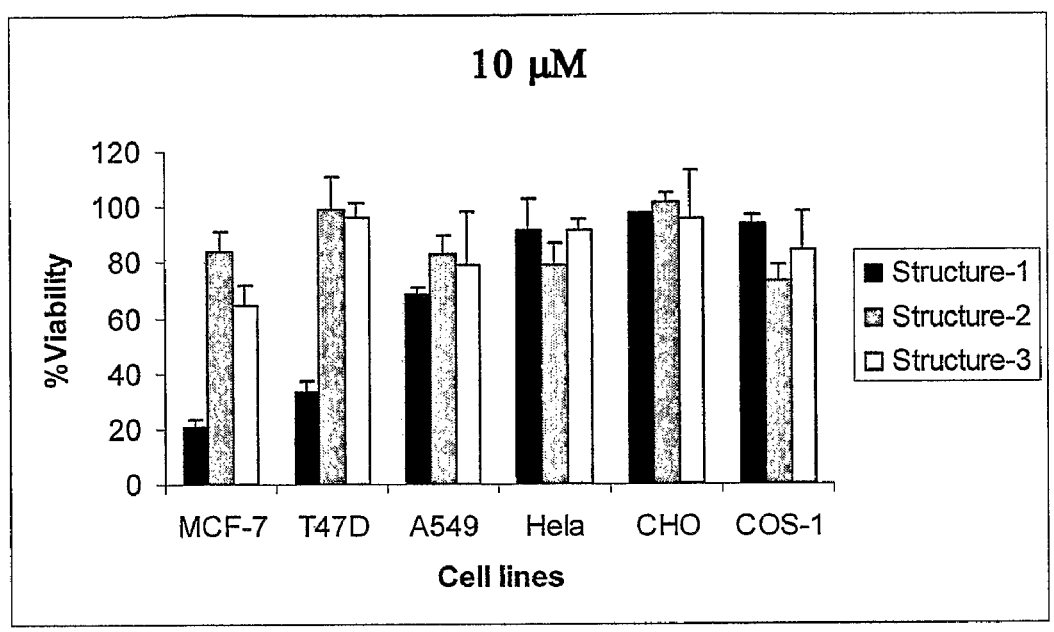
FIG. 6A summarizes the in vitro toxicity comparison of 10 μM of derivative 1, 2 and 3 (i.e., structures 1, 2, & 3) treated for 4 h in different cancer and non cancer cells. Following treatment the cells were washed and kept in serum media for 6 days and then assayed for viability with MTT.
FIG. 6B summarizes the in vitro toxicity comparison of 50 μM of derivative 1, 2 and 3 (i.e., structures 1, 2, & 3) treated for 4 h in different cancer and non cancer cells. Following treatment the cells were washed and kept in serum media for 6 days and then assayed for viability with MTT.
Figure 6:
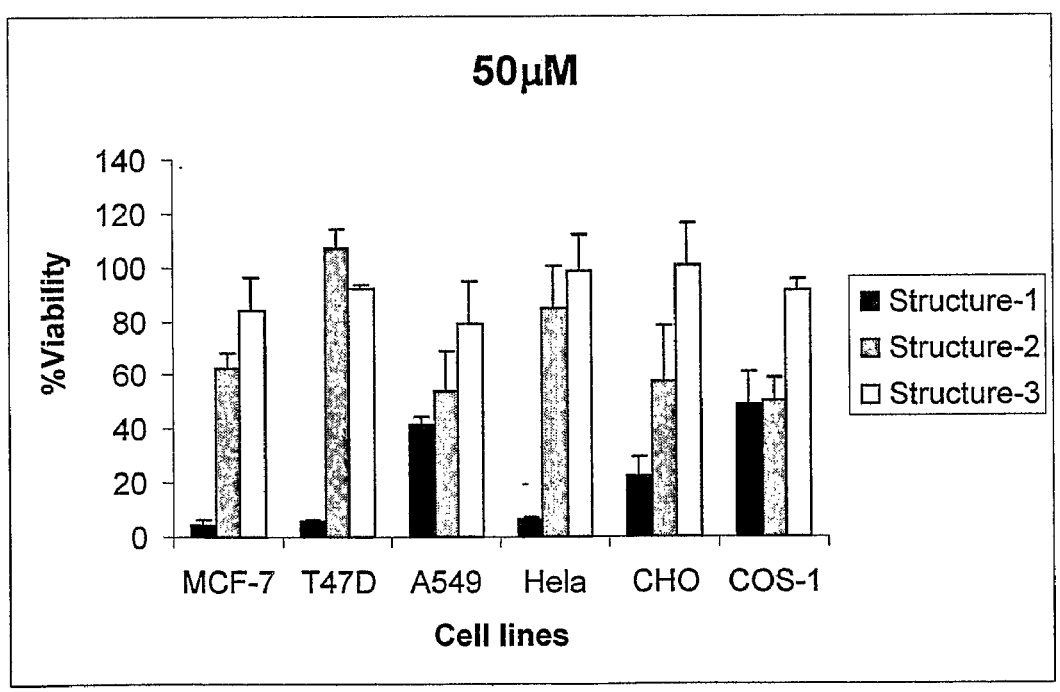
Figure 7:
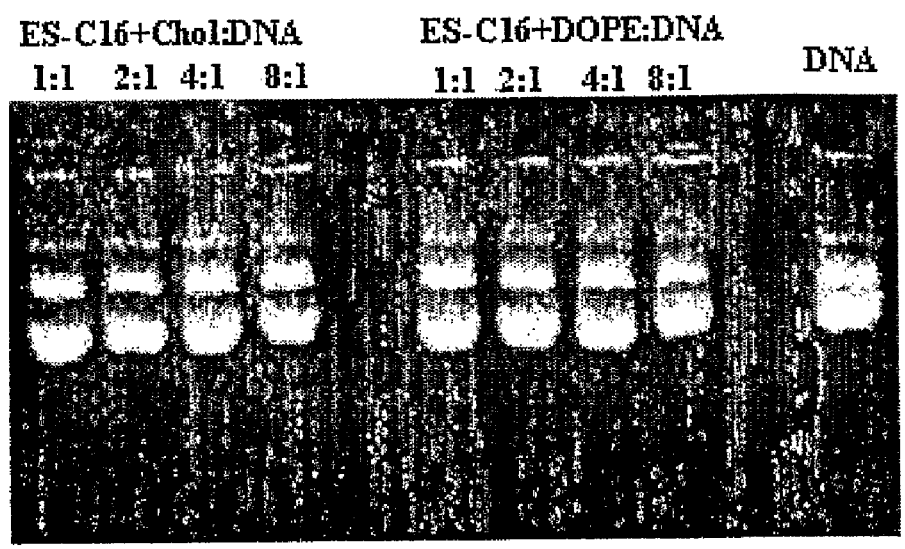
FIG. 7 depicts that novel cationic 17-α substituted estradiol-derivatives 2 & 3 (structures 2 & 3) in combination with co-lipid DOPE are showing partial to full DNA condensation property specifically at higher charge ratios of 4:1 and 8:1. Using co-lipid as cholesterol the DNA binding property of derivatives 2 & 3 are not observed in the given conditions.
Figure 7:
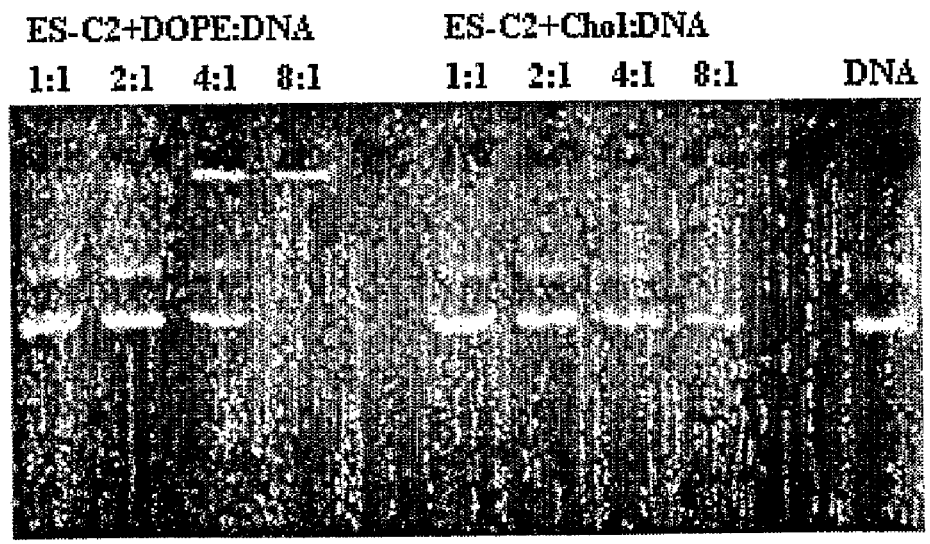

Structure of Representative Compounds 1, 2 and 3 of derivative A for 4 h, washed and kept in serum media for 6 days to observe cellular toxicity using MTT assay (FIGS. 1, 2, 4, 6A and 6B), except for one cell line where the assay was done after 4 days (FIG. 3). In another set of experiment, the cells were treated continuously for 48 h in presence of serum media and cellular toxicities were assayed promptly (FIG. 5). As is evident from FIGS. 1-3, the breast cancer cells showed less than 50% viability for an initial exposure of only 4 h of 10 µM derivative A. As is evident from FIG. 4, upon only 4 h exposure, 10 µM derivative A did not elicit toxicity to A549, Hela, CHO and COS-1 cells. This shows that the breast cancer cells which are directly/indirectly implicated with estrogen receptors were susceptible to undergo cell killing when derivative A was treated upon. MCF-7 and T47D are natural

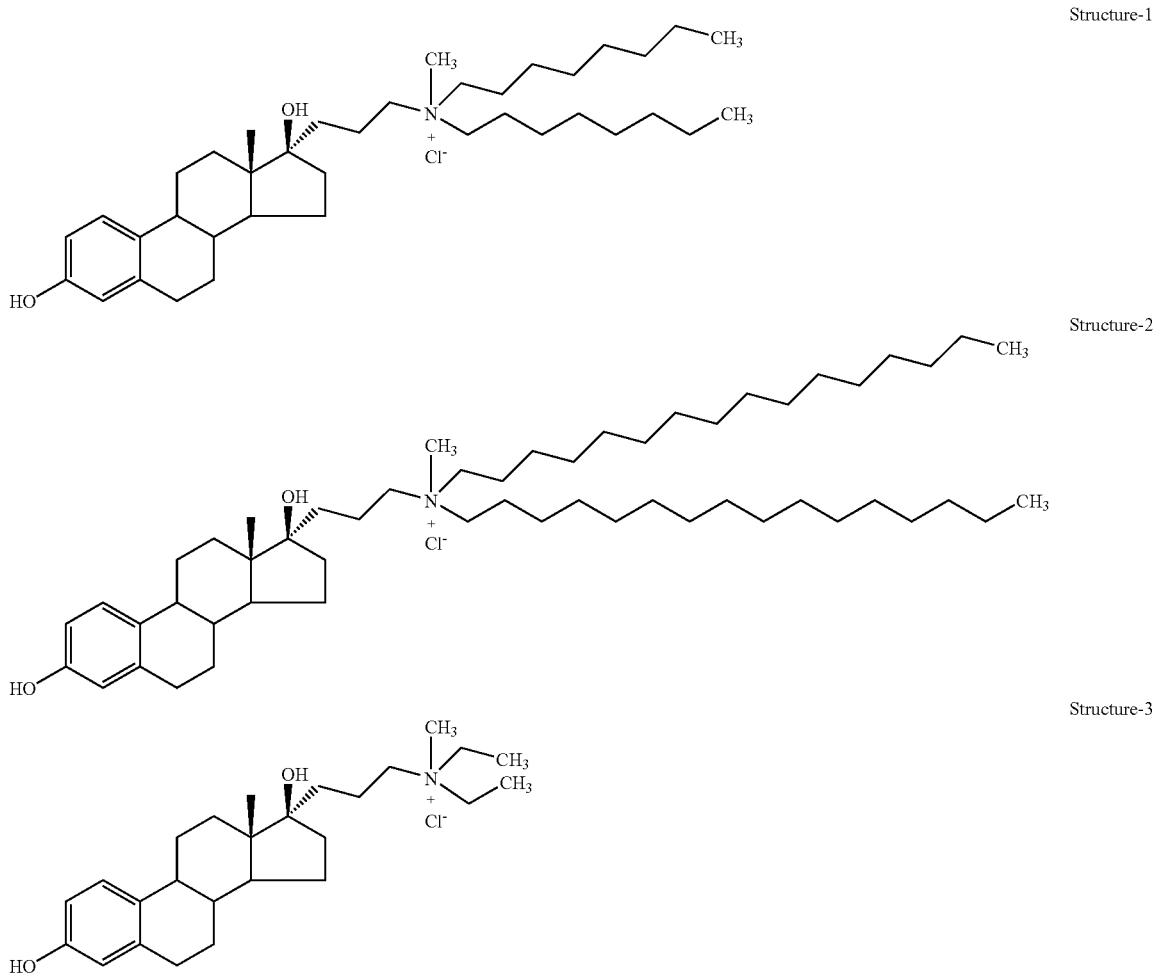

Cancer Cell Specific Anticancer Properties of the Presently Described Cationic Estradiol Derivative A:

The in vitro cytotoxicities of the derivative A to various cancer and non-cancer cells across different molar concentrations (0.5 µM-50 µM) were performed. The cancer cells were chosen from various origins, such as breast cancer cells MCF-7 (primary carcinoma), T47D (ductal carcinoma), MDA-MB-468 (secondary, metastatic); cervical cancer cell Hela; lung cancer cell A549 (metastatic). The non cancer cells that were chosen for this study were CHO (Chinese hamster ovary cells) and COS-1 (Monkey kidney cells). In one set of experiments, the cells were treated at different concentrations ER expressing breast cancer cells whereas MDA-MB-468 is a natural ER knockout breast cancer cell. But MDA-MB breast cancer cells upon estrogen exposure showed very interesting biochemical properties such as enhanced gene transfection (14-15), thereby showing that even though the ER expression is nil but the biochemical pathway that may utilize extraneous estrogen is still active in this cell line. So, estrogen or its derivatives such as derivative A does show some unexplained, biochemical phenomenon in certain breast cancer cells that do not express natural ER any more. So, the FIGS. 1-4 showed that even at low time of exposure of derivative A the breast cancer cells were the worst affected cells which are directly/indirectly implicated with ER.

In the second set of experiments, upon continuous exposure of 10 μM of derivative A for 48 h, not only the breast cancer cells but also cervical cancer cell Hela showed very low viability (FIG. 5). Even in the continuous treatment of 10 μM derivative A for 48 h, cancer cell A549 and non-cancer cell CHO showed no sign of toxicity. This set of results evidently pointed out that at continuous exposure of derivative A the cancer cells that are of gynecological origins i.e., breast, cervix etc. showed 50% or much less viability at even a miniscule concentration of 10 μM. Estrogen is a natural ligand which has direct/indirect role for normal growth of gynecological organs. Upon binding with ER estrogen can regulate several of the cancer up-regulating genes in breast and other gynecological cancers (1). So, it is quite natural that any derivative of estradiol may show targeted delivery into gynecological organs which are directly/indirectly implicated with ER. Our estradiol derivatives probably due to some unexplainable genetic regulation up-regulates anticancer activities in gynecological cancer cells alone, leaving non-gynecological cancer cells and non-cancer cells untouched.

Applications

The present invention can be exploited for treating gynecological cancers such as breast, cervical cancer etc. The lipid derivatives of this invention can also be used to deliver polyanions, polypeptides or nucleopolymers into cells via estrogen receptors only to cancer cells for the purpose of targeted healing. The cationic estrogen derivative disclosed herein can be used to deliver an expression vector into a cell for therapeutic use. The expression vectors can be used in gene therapy protocols to deliver a therapeutically useful protein to a cell or for delivering nucleic acids encoding therapeutically useful protein molecules. The invention i.e. cationic estradiol derivative can be formulated with anionic, zwitter-ionic and lipophilic therapeutic agents including adjuvant anticancer agents such as doxorubicin, a lipophilic compound, to obtain complexes comprising the invention derivatives and a therapeutic agent(s). In particular, the presently disclosed cationic estradiol derivatives hold potential for future exploitation in targeted, anticancer therapeutic modality to combat cancer. Cells and Cell Culture. CHO (Chinese hamster ovary), COS-1 (African Green monkey kidney cells) HeLa (Human cervical carcinoma), MCF-7 (Human breast primary adenocarcinoma), T47D (Human breast ductal carcinoma), MDA-MB-468 (Human breast secondary adenocarcinoma), and A-549 (Human lung carcinoma) cell lines were procured from the National Centre for Cell Sciences (NCCS), Pune, India and were mycoplasma free. Cells were cultured at 37° C. in Dulbecco's modified Eagle's medium (DMEM) [for MDA MB-468 cells, RPMI 1640 medium] with 10% Fetal Bovine serum, 50 μg/mL penicillin, 50 μg/mL streptomycin and 20 μg/mL kanamycin in a humidified atmosphere containing 5% $CO_2$. Cultures of 85-90% confluency were used for all of the experiments. The cells were trypsinized, counted, subcultured in 96-well plates for viability studies. The cells were allowed to adhere overnight before they were used for experiments.
Preparation of Samples and sample treatment. The cationic estradiol derivatives were dissolved in cell culture grade DMSO to get a primary stock. The stock is progressively diluted with DMSO to get secondary stocks. Finally, the working concentrations of the derivatives were obtained by adding the secondary DMSO stocks in 10% Fetal Bovine serum containing cell culture medium. The amount of DMSO in working solutions never exceeded more than 0.2% with respect to the serum containing culture medium. The 100 μl of cell culture solutions containing respective concentrations of cationic estradiol derivatives are given to cells pre-washed with Phosphate buffer saline. The cells were either kept in exposure with respective concentrations of estradiol derivatives for 4 h or 48 h. For 4 h treatment, the cells were washed and kept in presence of cell culture media without the working concentrations of estradiol derivatives for 4 or 6 days, as the case may be. The cells were then assayed for viability using MTT. For 48 h continuous treatment, the cells were washed and promptly assayed for viability using MTT.

The following examples are given by the way of illustration of the working of the invention in actual practice and therefore should not be read or construed to limit the scope of the invention.

Example 1

Synthesis of the Cationic Estradiol Derivative 1
(Scheme 1)

Step A: Synthesis of 3-tert butyldimethylsilyloxy Estrone

To a solution of estrone (a) (1 g, 3.69 mmoles) in dry DCM & dry DMF (9:1 v/v), 1.18 g (11.09 mmoles) of 2,6 Lutidine and 0.93 ml (4.06 mmoles) of TBDMS-triflate at 0° C. was added. The reaction mixture was stirred at room temperature for 30 min. The reaction mixture was taken in 20 ml of dichloromethane, washed with saturated $NaHCO_3$ solution (1×20 ml), water (2×20 ml) and brine (1×20 ml) The non-aqueous solvent was finally dried with anhydrous $Na_2SO_4$ and dried in vacuum. Column chromatographic purification (using 60-120 mesh silica gel and 2% ethyl acetate in hexane as eluting solvent mixture) of the dried residue afforded $a_1$ as a white solid (1.01 g, 71% yield, $R_f$ 0.4 in 10% ethyl acetate in hexane).

$^1$H NMR (300 MHz, $CDCl_3$): δ=0.19 [s, 6H, $Si(CH_3)_2$], 0.9 [s, 3H, 18-CH3], 1.0 [s, 9H, $SiC(CH_3)_3$], 1.4-1.7 and 1.9-2.55 [m, 13H, cyclopentane and cyclohexane ring protons], 2.85 [m, 2H, 6-$CH_2$], 6.52 [d, J=2.2 Hz, 1H, 4-CH], 6.57 [dd, J1=2.6 Hz and J2=8.4 Hz, 1H, 2-CH], 7.09 [d, J=8.4 Hz, 1H, 1-CH],
FABMS (LSIMS): m/z: 384 (observed mass), 384.62 (calculated mass) for $C_{24}H_{36}SiO_2$ Step B: Synthesis of 3-tert butyldimethylsilyloxy-17α-propenyl-17β-Estradiol To a mixture of Mg metal (300 mg, 12.57 mmoles) in dry THF (5 ml), 1,2-dibromoethane (catalytic amount) and Allyl bromide (1.07 ml, 12.57 mmoles) was added drop wise at 0° C. under Nitrogen atmosphere. The reaction mixture was stirred at room temperature for 30 min. To the above mixture $a_1$ (967 mg, 2.5 mmoles) dissolved in dry THF (10 ml) was added at 0° C. The reaction mixture was refluxed for 16 h. After the completion of the reaction the reaction mixture was quenched by adding saturated solution of Ammonium chloride solution (20 ml) at room temperature and subsequently extracted with ethyl acetate (2×25 ml). The organic layer was washed with water (2×50 ml), brine (1×50 ml) and finally dried with anhydrous $Na_2SO_4$. Column chromatographic purification (using 60-120 mesh silica gel and 4% ether in hexane as eluting solvent) of the residue afforded $a_2$ as a white solid (890 mg, 83% yield, $R_f$ 0.58 in 20% ether in hexane).

$^1$H NMR (300 MHz, $CDCl_3$): δ=0.19 [s, 6H, $Si(CH_3)_2$], 0.91 [s, 3H, 18-$CH_3$], 1.0 [s, 9H, $SiC(CH_3)_3$], 1.2-1.7 & 2.05-2.4 [m, 13H, cyclopentane and cyclohexane ring protons], 1.85-2.0 [dm, 2H, —CH$_2$—CH=CH$_2$] 2.85 [m, 2H, 6-CH$_2$], 5.1-5.32 [dd, 2H, CH=CH$_2$], 5.95 [m, 1H, CH=CH$_2$], 6.52 [d, 1H, 4-CH], 6.57 [dd, 1H, 2-CH] 7.09 [d, 1H, 1-CH], FABMS (LSIMS): m/z: 426 (observed mass), 426.71 (calculated mass) for $C_{27}H_{42}SiO_2$

Step C: Synthesis of 3-tert-butyldimethylsilyloxy-17α-[3-hydroxypropane]-17β-estradiol To a stirred THF (5 ml) solution of 17α-propenyl-β-Estradiol (890 mg, 2.09 mmole), borane in DMS (97% solution, 0.3 ml, 4.28 mmoles) was added at 0° C. and stirred under nitrogen for 6 h. A solution of 3N NaOH (6 ml) and H$_2$O$_2$ (4.5 ml, 30% w/v) was added at 0° C. and the mixture was warmed to room temperature. The resulting mixture was then quenched by water, and extracted with ethyl acetate (2×20 ml). Organic layer was washed with water (2×25 ml), brine (1×25 ml), finally dried over anhydrous Na$_2$SO$_4$ and evaporated under vacuum. The crude compound was purified by column chromatography with hexane/ethyl acetate (80:20) as eluting solvent mixture to give 481 mg (51.25%) of Alcohol (a$_3$).

$^1$H NMR (300 MHz, CDCl$_3$): δ=0.19 [s, 6H, Si(CH$_3$)$_2$], 0.91 [s, 3H, 18-CH3], 0.99 [s, 9H, SiC(CH$_3$)$_3$], 1.2-2.3 [m, 17H, cyclopentane, cyclohexane ring protons & 17□-CH$_2$CH$_2$—CH$_2$—OH], 2.80 [m, 2H, 6-CH$_2$], 3.6-3.75 [dm, 2H, 17□-CH$_2$CH$_2$—CH$_2$—OH], 6.50 [s, 1H, 4-CH], 6.55 [d, 1H, 2-CH] 7.05 [d, 1H, 1-CH].

FABMS (LSIMS): m/z: 444 (observed mass), 443.72 (calculated mass) for $C_{27}H_{43}SiO_3$

Step D: Synthesis of 3-tert-butyldimethylsilyloxy-17α-[3-aldehydo propane]-17β-estradiol To a cooled (−78° C., acetone dry ice both) solution of Oxalyl chloride (205 mg, 1.62 mmoles), in dichloromethane (10 mL), dry dimetyl sulfoxide (252 mg, 3.24 mmoles) was added drop wise and the resulting mixture was stirred for 15 min and alcohol (480 mg, 1.018 mmoles) dissolved in dichlromethane (5 mL) was added drop wise at −78° C. The mixture was stirred for 30 min, triethylamine (654 mg, 12.57 mmoles) was added drop wise and the resultant mixture gradually warmed to room temperature over 2 h. The mixture was quenched with water (50 mL) extracted with dichloromethane (50×3), washed with brine, driedover anhydrous sodium sulfate, filtered and concentrated in vacuum. The crude product (a$_4$) was continued for next reaction without any further purification.

Step E: Synthesis of 3-tert-butyldimethylsilyloxy-17α-[3-N,Ndioctyl(amino) propane]-17β-estradiol The crude aldehyde (a$_4$) prepared above (400 mg, 0.904 mmoles) and N,N-dioctylamine (218 mg, 0.904 mmoles) was dissolved in 10 mL dichloromethane and was stirred for 0.5 h under nitrogen in room temperature. Sodium cyanoborohydride (329 mg, 4.52 mmoles) was added to the reaction mixture and the stirring was continued further for 24 h under nitrogen atmosphere. The reaction mixture was concentrated and the residue upon column chromatographic purification (using 60-120 mesh size silica gel and hexane/ethyl acetate (80:20) as eluent) afforded the title compound (a$_5$), 100 mg (25.2%) as semisolid.

$^1$H NMR (300 MHz, CDCl$_3$): δ=0.19 [s, 6H, Si(CH$_3$)$_2$], 0.87-0.93 [m, 9H, 18-CH3, N—(CH$_2$—(CH$_2$)$_6$—CH$_3$)$_2$], 0.99 [s, 9H, SiC(CH$_3$)$_3$], 1.2-2.3 [m, 41H, cyclopentane, cyclohexane ring protons, 17α-CH$_2$CH$_2$—CH$_2$—N—(CH$_2$—(CH$_2$)$_6$—CH$_3$)$_2$], 2.72-2.84 [m, 8H, 6-CH$_2$, 17α-CH$_2$CH$_2$—CH$_2$—N—(CH$_2$—(CH$_2$)$_6$—CH$_3$)$_2$], 6.50 [s, 1H, 4-CH], 6.55 [d, 1H, 2-CH] 7.05 [d, 1H, 1-CH].

FABMS (LSIMS): m/z: 669 (observed mass), 668.16 (calculated mass) for $C_{43}H_{77}SiO_2N$

Step F: Synthesis of 3-tert-butyldimethylsilyloxy-17α-[3-N,N-dioctyl(methyl)aminopropane]-17βEstradiol Compound (a$_5$) obtained in step F (100 mg, 0.149 mmoles) was treated with excess methyl iodide (3 mL), in (4 mL) dichloromethane+methanol (1:1) and stirred for 3 h at room temperature. The reaction mixture was concentrated and the residue upon column chromatographic purification (using 100-200 mesh size silica gel and 2% methanol in chloroform as eluent) offered the title compound (a$_6$), 80 mg (80%) as light yellow solid.

$^1$H NMR (200 MHz, CDCl$_3$): δ=0.19 [s, 6H, Si(CH$_3$)$_2$], 0.87-0.93 [m, 9H, 18-CH3, N—(CH$_2$—(CH$_2$)$_6$—CH$_3$)$_2$], 0.99 [s, 9H, SiC(CH$_3$)$_3$], 1.2-2.3 [m, 41H, cyclopentane, cyclohexane ring protons, 17α-CH$_2$CH$_2$—CH$_2$—N—(CH$_2$—(CH$_2$)$_6$—CH$_3$)$_2$], 2.84 [m, 2H, 6-CH$_2$], 3.3-3.6 [m, 9H, CH$_2$—N$^+$ & CH$_3$—N$^+$], 6.50 [s, 1H, 4-CH], 6.55 [d, 1H, 2-CH] 7.05 [d, 1H, 1-CH].

Step G: Synthesis of 17α-[3-N,N-dioctyl(methyl) aminopropane]-17β-Estradiol (Structure 1 in Scheme 1)

Compound (a$_6$) (80 mg, 0.1173 mmoles) was dissolved in THF (2 mL), excess tetrabutyl ammonium fluoride in THF (2 mL) was added at 0° C. and stirred for 6 h under nitrogen atmosphere. The mixture was quenched with water (15 mL) extracted with dichloromethane (25×3), washed with brine, dried over anhydrous sodium sulfate, filtered and concentrated in vacuum. The crude product was purified by column chromatography using 60-120 mesh silica gel, methanol:chloroform as eluent, followed by chloride ion exchange in Amberlyst A-26 using methanol as eluent to give 37 mg (46.25%) of compound 1.

$^1$H NMR (200 MHz, CDCl$_3$): δ=0.87-0.93 [m, 9H, 18-CH3, N—(CH$_2$—(CH$_2$)$_6$—CH$_3$)$_2$], 1.2-2.3 [m, 41H, cyclopentane, cyclohexane ring protons, 17α-CH$_2$CH$_2$—CH$_2$—N—(CH$_2$—(CH$_2$)$_6$—CH$_3$)$_2$], 2.84 [m, 2H, 6-CH$_2$], 3.0 [S, 3H, CH$_3$—N$^+$], 3.2 [m, 6H, CH$_2$—N$^+$] 6.50 [s, 1H, 4-CH], 6.55 [d, 1H, 2-CH] 7.05 [d, 1H, 1-CH].

ESI-MS: m/z: 568 (observed mass), 566.94 (calculated mass) for $C_{38}H_{64}O_2N$

Example 2

Synthesis of the Cationic Estradiol Derivative 2

Steps A-D are same as shown for the synthesis of derivative 1 (or structure 1).

Step E: Synthesis of 3-tertbutyldimethylsilyloxy-17α-[3N,Ndihexadecyl (amino)propane]-17β-estradiol The crude aldehyde prepared in the step-D (in Example-1), (500 mg, 1.13 mmoles) and N,N-di-octadecylylamine (558 mg, 1.4 mmoles) was dissolved in 10 mL dichloromethane and was stirred for 0.5 h under nitrogen in room temperature. Sodium cyanoborohydride (283 mg, 4.50 mmoles) was added to the reaction mixture and the stirring was continued further for 24 h under nitrogen atmosphere. The reaction mixture was concentrated and the residue upon column chromatographic purification (using 60-120 mesh size silica gel and hexane/ethyl acetate (80:20) as eluent) afforded the title compound, 321 mg (57.3%) as semisolid.

$^1$H NMR (300 MHz, CDCl$_3$): δ=0.19 [s, 6H, Si(CH$_3$)$_2$], 0.87-0.93 [m, 9H, 18-CH3, N—(CH$_2$—(CH$_2$)$_{14}$—C$\underline{H}_3$)$_2$], 0.99 [s, 9H, SiC(CH$_3$)$_3$], 1.2-2.3 [m, 73H, cyclopentane, cyclohexane ring protons, 17α-CH$_2$CH$_2$—CH$_2$—N—(CH$_2$—(CH$_2$)$_{14}$—CH$_3$)$_2$], 2.72-2.84 [m, 8H, 6-CH$_2$, 17α-CH$_2$CH$_2$—CH—N—(CH$_2$—(CH$_2$)$_{14}$—C$\underline{H}_3$)$_2$], 6.50 [s, 1H, 4-C$\underline{H}$], 6.55 [d, 1H, 2-C$\underline{H}$] 7.05 [d, 1H, 1-C$\underline{H}$].

FABMS (LSIMS): m/z: 893 (observed mass), 892.54 (calculated mass) for C$_{59}$H$_{109}$SiO$_2$N

Step F: Synthesis of 3-tert-butyldimethylsilyloxy-17α-[3-N,N-dihexadecyl(methyl)aminopropane]-17βEstradiol Compound obtained in step-E (300 mg, 0.335 mmoles) was treated with excess methyl iodide (3 mL), in (4 mL) dichloromethane+methanol (1:1) and stirred for 3 h at room temperature. The reaction mixture was concentrated and the residue upon column chromatographic purification (using 100-200 mesh size silica gel and 2% methanol in chloroform as eluent) offered the title compound (a$_6$), 170 mg (56.6%) as light yellow solid.

$^1$H NMR (200 MHz, CDCl$_3$): δ=0.19 [s, 6H, Si(CH$_3$)$_2$], 0.87-0.93 [m, 9H, 18-CH3, N—(CH$_2$—(CH$_2$)$_{14}$—C$\underline{H}_3$)$_2$], 0.99 [s, 9H, SiC(CH$_3$)$_3$], 1.2-2.3 [m, 73H, cyclopentane, cyclohexane ring protons, 17α-CH$_2$CH$_2$—CH$_2$—N—(CH$_2$—(CH$_2$)$_{14}$—CH$_3$)$_2$], 2.84 [m, 2H, 6-C$\underline{H}_2$], 3.3-3.6 [m, 9H, CH$_2$—N$^+$ & CH$_3$—N$^+$], 6.50 [s, 1H, 4-C$\underline{H}$], 6.55 [d, 1H, 2-C$\underline{H}$] 7.05 [d, 1H, 1-C$\underline{H}$].

Step G: Synthesis of 17α-[3-N,N-dihexadecyl(methyl)aminopropane]-17β-Estradiol (Structure 2 or Derivative 2)

Compound obtained above (100 mg, 0.11 mmoles) was dissolved in THF (2 mL), excess tetrabutyl ammonium fluoride in THF (2 mL) was added at 0° C. and stirred for 6 h under nitrogen atmosphere. The mixture was quenched with water (15 mL) extracted with dichloromethane (25×3), washed with brine, dried over anhydrous sodium sulfate, filtered and concentrated in vacuum. The crude product was purified by column chromatography using 60-120 mesh silica gel, methanol:chloroform as eluent, followed by chloride ion exchange in Amberlyst A-26 using methanol as eluent to give 60 mg (60.0%) of structure-2.

$^1$H NMR (200 MHz, CDCl$_3$): δ=0.87-0.93 [m, 9H, 18-CH3, N—(CH$_2$—(CH$_2$)$_{14}$—CH$_3$)$_2$], 1.2-2.3 [m, 73H, cyclopentane, cyclohexane ring protons, 17α-CH$_2$CH$_2$—CH$_2$—N—(CH$_2$—(CH$_2$)$_{14}$—CH$_3$)$_2$], 2.84 [m, 2H, 6-C$\underline{H}_2$], 3.0 [S, 3H, CH$_3$—N$^+$], 3.2 [m, 6H, CH$_2$—N$^+$] 6.50 [s, 1H, 4-CH], 6.55 [d, 1H, 2-CH] 7.05 [d, 1H, 1-CH].

ESI-MS: m/z: 792 (observed mass), 791.36 (calculated mass) for C$_{54}$H$_{96}$O$_2$N

Example 3

Synthesis of the Cationic Estradiol Derivative 3

Steps A-D are same as shown for the synthesis of derivative 1 (or structure 1).

Step E: Synthesis of 3-tertbutyldimethylsilyloxy-3N, N-diethyl(methyl)aminopropane-17β-estradiol The crude aldehyde prepared in step-E (in example 1), (500 mg, 1.13 mmoles) and N,N-di-ethyl amine (90 mg, 1.23 mmoles) was dissolved in 10 mL dichloromethane and was stirred for 0.5 h under nitrogen in room temperature. Sodium cyanoborohydride (283 mg, 4.50 mmoles) was added to the reaction mixture and the stirring was continued further for 24 h under nitrogen atmosphere. The reaction mixture was concentrated and the residue upon column chromatographic purification (using 60-120 mesh size silica gel and hexane/ethyl acetate (80:20) as eluent) afforded the title compound, 180 mg (36.01%) as semisolid.

$^1$H NMR (300 MHz, CDCl$_3$): δ=0.19 [s, 6H, Si(CH$_3$)$_2$], 0.87-0.93 [m, 9H, 18-CH3, N—(CH$_2$—CH$_3$)$_2$], 0.99 [s, 9H, SiC(CH$_3$)$_3$], 1.2-2.3 [m, 16H, cyclopentane, cyclohexane ring protons, 17α-CH$_2$CH$_2$—CH$_2$—N—(CH$_2$—CH$_3$)$_2$], 2.72-2.84 [m, 8H, 6-C$\underline{H}_2$, 17α-CH$_2$CH$_2$—CH$_2$—N—(CH$_2$—CH$_3$)$_2$], 6.50 [s, 1H, 4-C$\underline{H}$], 6.55 [d, 1H, 2-C$\underline{H}$] 7.05 [d, 1H, 1-C$\underline{H}$].

Step F: Synthesis of 3-tert-butyldimethylsilyloxy-17α-[3-N,N-diethyl(methyl) aminopropane]-17βEstradiol Compound obtained in step-E (180 mg, 0.36 mmoles) was treated with excess methyl iodide (3 mL), in (4 mL) dichloromethane+methanol (1:1) and stirred for 3 h at room temperature. The reaction mixture was concentrated and the residue upon column chromatographic purification (using 100-200 mesh size silica gel and 2% methanol in chloroform as eluent) offered the title compound (a$_6$), 120 mg (66.6%) as light yellow solid.

$^1$H NMR (200 MHz, CDCl$_3$): δ=0.19 [s, 6H, Si(CH$_3$)$_2$], 0.87-0.93 [m, 9H, 18-CH3, N—(CH$_2$—CH$_3$)$_2$], 0.99 [s, 9H, SiC(CH$_3$)$_3$], 1.2-2.3 [m, 16H, cyclopentane, cyclohexane ring protons, 17α-CH$_2$CH$_2$—CH$_2$—N—(CH$_2$—CH$_3$)$_2$], 2.84 [m, 2H, 6-CH$_2$], 3.3-3.6 [m, 9H, CH$_2$—N$^+$ & CH$_3$—N$^+$], 6.50 [s, 1H, 4-C$\underline{H}$], 6.55 [d, 1H, 2-C$\underline{H}$] 7.05 [d, 1H, 1-C$\underline{H}$].

ESI-MS: m/z: 515 (observed mass), 514 (calculated mass) for C$_{32}$H$_{55}$SiO$_2$N

Step G: Synthesis of 17α-[3-N,N-diethyl(methyl) aminopropane]-17β-Estradiol (Structure 3 or Derivative 3)

Compound obtained above (120 mg, 0.233 mmoles) was dissolved in THF (2 mL), excess tetrabutyl ammonium fluoride in THF (2 mL) was added at 0° C. and stirred for 6 h under nitrogen atmosphere. The mixture was quenched with water (15 mL) extracted with dichloromethane (25×3), washed with brine, dried over anhydrous sodium sulfate, filtered and concentrated in vacuum. The crude product was purified by column chromatography using 60-120 mesh silica gel, methanol:chloroform as eluent, followed by chloride ion exchange in Amberlyst A-26 using methanol as eluent to give 72 mg (60.0%) of structure-3.

$^1$H NMR (200 MHz, CDCl$_3$): δ=0.87-0.93 [m, 9H, 18-CH3, N—(CH$_2$—CH$_3$)$_2$], 1.2-2.3 [m, 16H, cyclopentane, cyclohexane ring protons, 17α-CH$_2$CH$_2$—CH$_2$—N—(CH$_2$—CH$_3$)$_2$], 2.84 [m, 2H, 6-CH$_2$], 3.0 [S, 3H, CH$_3$—N$^+$], 3.2 [m, 6H, CH$_2$—N$^+$] 6.50 [s, 1H, 4-CH], 6.55 [d, 1H, 2-CH] 7.05 [d, 1H, 1-CH].

ESI-MS: m/z: 382 (observed mass), 400.62 (calculated mass) for C$_{26}$H$_{42}$O$_2$N Example 4

Percent Cell Viabilities

Cytotoxicities of the cationic estradiol derivative 1 were evaluated by the 3-(4,5-dimethylthiazol-2-yl)-2,5-diphenyltetrazolium bromide (MTT) reduction assay. The assay was performed in 96-well plates. Depending on the duration of experiment 8000-15000 cells were plated in 96 well plates and kept overnight. After say, 12 h when the cells were adhered to the bottom of plates the solutions containing respective concentrations of derivative 1 were added to triplicate wells. The treatment of derivative 1 to the cells was for either 4 h or 48 h as mentioned earlier. For 4 h treatment the cells were washed and are either kept for 4 days or 6 days in serum media and then MTT was added to the cells. For 48 h treatment, the cells were promptly washed and then MTT was added to the cells. Results were expressed as percent viability=[A$_{540}$(treated cells)–background/A$_{540}$(untreated cells)–background]×100. FIG. 1-6 summarizes the results of the MTT based cell viability assays for 1 across the varying concentrations and cells of different origins.

Example 5

DNA Binding Assay

The DNA binding abilities of the 17-α substituted estradiol-derivatives 2 & 3 (structures 2 & 3) were assessed by their gel retardation assay on a 0.8% agarose gel. 0.40 µg of pCMV-SPORT-□gal was complexed with the cationic estradiol derivatives (at a cationic estradiol derivatives:DNA charge ratio 8:1, 4:1, 2:1 and 1:1) in a total volume of 16 µl of HEPES buffer (pH 7.4) and incubated at room temperature for 30 min on a rotary shaker. 3 µl of 6× loading buffer (0.25% bromophenol blue, 40% sucrose) was added to it, and total solution was loaded to each well. The samples were electrophoresed at 80 V for approximately 2 h and the DNA bands were visualized by staining for 30 min with ethidium bromide solution followed by 30 min destaining in water.

We claim:
1. A cationic estradiol compound of formula A:

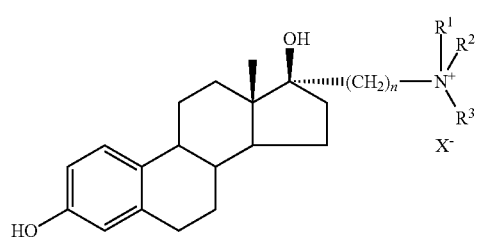

wherein:
each of R$^1$ and R$^2$ is independently hydrogen or a lipophilic moiety selected from the group consisting of a saturated alkyl chain, and a mono-, di- or tri-unsaturated alkenyl chain, each containing from 2 to 22 carbons, provided both R$^1$ and R$^2$ are not hydrogen;
R$^3$ is independently a C$_1$-C$_5$ straight or branched chain alkyl group;
n is an integer from 2 to 7; and
X is selected from chlorine, bromine and iodine atom.

2. The compound of claim 1, wherein both R$^1$ and R$^2$ are lipophilic moieties selected from the group consisting of a saturated alkyl chain, and a mono-, di- or tri-unsaturated alkenyl chain, each containing from 2 to 22 carbons.

3. The compound of claim 1, wherein R$^1$ is hydrogen; and R$^2$ is a lipophilic moiety selected from the group consisting of a saturated alkyl chain, and a mono-, di- or tri-unsaturated alkenyl chain, each containing from 2 to 22 carbons.

4. The compound of claim 1, wherein the compounds of formula A are as follows:
17α-(3-(N,N-dioctyl-N-methyl-amino)-propan-1-yl)-estradiol (1);
17α-(3-(N,N-dihexadecyl-N-methyl-amino)-propan-1-yl)-estradiol (2);
17α-(3-(N,N-diethyl-N-methyl-amino)-propan-1-yl)-estradiol (3); and
X, in each case, is selected from chlorine, bromine and iodine atoms.

5. A pharmaceutical composition comprising:
a. a cationic estradiol compound of formula A:

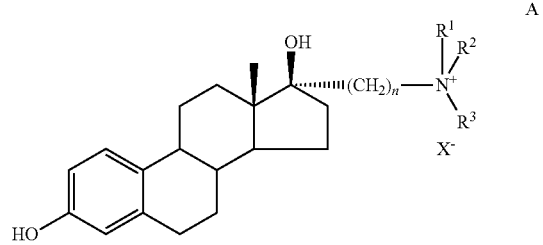

wherein:
each of R$^1$ and R$^2$ is independently hydrogen or a lipophilic moiety selected from the group consisting of a saturated alkyl chain, and a mono-, di- or tri-unsaturated alkenyl chain, each containing from 2 to 22 carbons, provided both R$^1$ and R$^2$ are not hydrogen;
R$^3$ is independently a C$_1$-C$_5$ straight or branched chain alkyl group;
n is an integer from 2 to 7; and
X is selected from chlorine, bromine and iodine atom;
b. a co-lipid, and
c. a polyanionic compound optionally along with a pharmaceutically acceptable carrier, adjuvant and additives.

6. The composition of claim 5, wherein the molar ratio of cationic estradiol compound of formula A to co-lipid is about 1:1.

7. The composition of claim 5, wherein the molar ratio of total lipid comprising cationic estradiol compound of formula A and co-lipid to polyanionic compound is in the range of 1:1 to 8:1.

8. The composition of claim 5, wherein the co-lipid in step (b) is selected from cholesterol, dioleoylphosphatidylethanol-amine (DOPE), and dioleoylphosphatidylcholine (DOPC).

9. The composition of claim 5, wherein the polyanionic compound is selected from ribosomal RNA, antisense polynucleotide of RNA or DNA, and polynucleotide of genomic DNA, cDNA or mRNA.

10. A process for the synthesis of a cationic estradiol compound of formula A:

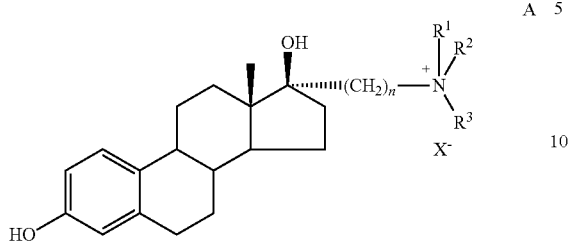

wherein:
each of $R^1$ and $R^2$ is independently hydrogen or a lipophilic moiety selected from the group consisting of a saturated alkyl chain, and a mono-, di- or tri-unsaturated alkenyl chain, each containing from 2 to 22 carbons, provided both $R^1$ and $R^2$ are not hydrogen;
$R^3$ is independently a $C_1$-$C_5$ straight or branched chain alkyl group;
n is the integer 3; and
X is selected from chlorine, bromine and iodine atom;
the process comprising the steps of:
(a) reacting 3-tert-butyldimethylsilyloxy-17α-(propan-3-al-1-yl)-estradiol with a mono- or di-alkyl amine of formula $NHR^1R^2$, in the presence of sodium cyanoborohydride, in a dry organic solvent, to obtain the corresponding secondary or tertiary amine;
(b) reacting the corresponding secondary or tertiary amine of step (a) with an alkyl halide of formula $R^3X$ in an organic solvent to obtain a tertiary or quaternary amine, wherein the quaternization of the intermediate tertiary amine is carried out at a temperature between –10° C. to 50° C.; and
(c) deprotecting the tert-butyldimethylsilyloxy group of the tertiary or quaternary amine obtained in step (b), followed by ion exchange chromatography using a halide ion exchange resin to obtain the cationic estradiol compound of formula A.

11. The process of claim 10, wherein the mono or di-alkyl amine of formula $NHR^1R^2$ in step (b) has a saturated or unsaturated aliphatic hydrocarbon chain.

12. The process of claim 10, wherein the saturated or unsaturated aliphatic hydrocarbon chain of mono or di-alkyl amine of formula $NHR^1R^2$ used in step (b) is selected from $C_2$ to $C_{22}$ hydrocarbon chain.

13. The process of claim 10, wherein the organic solvent in step (b) is selected from dichloromethane, methanol, and a mixture thereof.

14. The process of claim 10, wherein the alkyl halide in step (b) is selected from $C_1$ to $C_5$ alkyl halides.

15. The process of claim 10, wherein the halide ion exchange resins in step (c) is selected from chloride, bromide, and iodide ion exchange resins.

16. The process of claim 10, wherein the compounds of formula A obtained are as follows:
17α-(3-(N,N-dioctyl-N-methyl-amino)-propan-1-yl)-estradiol (1);
17α-(3-(N,N-dihexadecyl-N-methyl-amino)-propan-1-yl)-estradiol (2); and
17α-(3-(N,N-diethyl-N-methyl-amino)-propan-1-yl)-estradiol (3);
and X, in each case, is selected from chlorine, bromine and iodine atoms.

* * * * *